United States Patent
Stokes et al.

(10) Patent No.: US 7,871,963 B2
(45) Date of Patent: Jan. 18, 2011

(54) TUNABLE SURFACTANTS FOR OIL RECOVERY APPLICATIONS

(75) Inventors: Kristoffer K. Stokes, Jamaica Plain, MA (US); David Soane, Chestnut Hill, MA (US); Michael C. Berg, Somerville, MA (US); Kevin T. Petersen, Arlington, MA (US); William A. Mowers, Lynn, MA (US)

(73) Assignee: Soane Energy, LLC, Cambridge, MA (US)

( * ) Notice: Subject to any disclaimer, the term of this patent is extended or adjusted under 35 U.S.C. 154(b) by 0 days.

(21) Appl. No.: 11/850,749

(22) Filed: Sep. 6, 2007
(Under 37 CFR 1.47)

(65) Prior Publication Data

US 2008/0217013 A1 Sep. 11, 2008

Related U.S. Application Data

(60) Provisional application No. 60/843,815, filed on Sep. 12, 2006.

(51) Int. Cl.
| C09K 8/68 | (2006.01) |
| C09K 8/584 | (2006.01) |
| C09K 8/60 | (2006.01) |
| E21B 43/27 | (2006.01) |

(52) U.S. Cl. .................. 507/203; 507/206; 507/233; 507/260; 507/261; 166/300

(58) Field of Classification Search ............... 507/203, 507/206, 233, 260, 261, 263; 166/300
See application file for complete search history.

(56) References Cited

U.S. PATENT DOCUMENTS

| 3,107,726 | A | | 10/1963 | Greenwald |
| 3,956,261 | A | * | 5/1976 | Lin ........................... 530/502 |
| 4,296,812 | A | | 10/1981 | Kalfoglou |
| 4,391,925 | A | | 7/1983 | Mintz et al. |
| 5,200,096 | A | | 4/1993 | Williams et al. |
| 5,215,596 | A | | 6/1993 | Van Slyke |
| 5,406,019 | A | | 4/1995 | Dean |
| 5,482,118 | A | | 1/1996 | Clough |
| 6,172,204 | B1 | | 1/2001 | Sarkanen et al. |
| 6,484,441 | B1 | * | 11/2002 | Huttermann et al. ...... 47/58.1 R |
| 6,593,506 | B1 | | 7/2003 | Searle |
| 6,772,838 | B2 | * | 8/2004 | Dawson et al. ........... 166/280.1 |
| 2005/0038128 | A1 | | 2/2005 | Argillier et al. |
| 2006/0149109 | A1 | | 7/2006 | Ruziska et al. |
| 2006/0276345 | A1 | * | 12/2006 | Todd et al. .................. 507/203 |

FOREIGN PATENT DOCUMENTS

RU 2265473 C1 12/2005

OTHER PUBLICATIONS

U.S. Appl. No. 11/853,504.

* cited by examiner

*Primary Examiner*—Timothy J. Kugel
*Assistant Examiner*—Atnaf Admasu
(74) *Attorney, Agent, or Firm*—Elmore Patent Law Group, P.C.; Mahreen Chaudhry Hoda; Carolyn S. Elmore

(57) ABSTRACT

The systems and methods described herein provide for modified lignins and other compositions that may be useful as surfactants. These compositions have particular utility for energy-related applications. In embodiments, they may be useful for enhanced oil recovery. In embodiments, they may be useful for extracting bitumen from oil sands. In embodiments, they may be useful for environmental remediation.

22 Claims, No Drawings

TUNABLE SURFACTANTS FOR OIL RECOVERY APPLICATIONS

RELATED APPLICATION

This application claims the benefit of U.S. Provisional Application No. 60/843,815, filed on Sep. 12, 2006. The entire teachings of the above application are incorporated herein by reference.

FIELD OF APPLICATION

This application relates generally to surfactant compositions useful for applications in the energy industry involving petroleum production and environmental remediation.

BACKGROUND

As world-wide energy needs continue to grow, there is concern that demand for energy may outstrip its supply. Technologies for improving the efficiencies of petroleum production become increasingly valuable. Moreover, in light of the impact of petroleum production on the environment, technologies for environmental remediation are also desirable.

Oil extraction from deposits in source rock presently takes place in stages. Typically, the initial stage, known as primary recovery, involves drilling a hole from the surface to a subsurface reservoir, where oil is trapped under pressure. This hole may be known as a well or a wellbore. A subsurface oil reservoir is understood to be an underground pool of a liquid mix of hydrocarbons and other impurities that is contained within a geological formation beneath the surface of the earth. The subsurface reservoir may be penetrated by one or more wells, perforations that contact the subsurface reservoir and permit the removal of the liquid and gas hydrocarbons resident therein. When an oil reservoir containing oil under pressure is tapped by a drill hole, the reservoir's pressure forces its contents through the drill hole to the surface for collection. This process may continue until the pressure within the reservoir is no longer sufficient to expel the oil contained therein. When the pressure in the reservoir is depleted but there is still oil available, pumps may be used to bring the oil to the surface.

The wells used for removing the contents of the reservoir may also be used for injecting substances into the reservoir to enhance the extraction of its contents. For example, such materials as water, brine, steam, and mobilization chemicals such as surfactants may be injected. A well from which oil is recovered is known as a production well. A well through which substances are injected is known as an injection well.

Injection techniques are particularly useful when the pressure within the reservoir decreases so that supplemental measures are useful to increase the recovery of oil contained within the reservoir. Techniques used under these circumstances may be termed secondary recovery techniques. For example, the pressure within the reservoir may be increased by injecting water, steam or gas into the reservoir. Injecting water into a well to increase recovery of oil is called "waterflood." Other secondary recovery techniques may include flooding with polymers, alkali, or other chemical solutions, and various thermal processes. Alternatively, gases such as carbon dioxide, natural gas or nitrogen may be injected into the reservoir, where they expand and push additional oil out through the production wellbores, and where they may affect the viscosity of the remaining oil, thereby improving its flow rate on egress. The combination of primary and secondary oil recovery only removes a certain amount of the total oil content from an oil reservoir, approximately between 20% and 80%.

Hence, a large amount of the original oil remains in the reservoir after secondary recovery techniques. In large oil fields, over a billion barrels of oil may remain after secondary recovery efforts. The percentage of unrecovered hydrocarbons is largest in oil fields with complex lithologies, and the petroleum fractions left behind tend to be the heavier hydrocarbon materials and those liquid materials that may be trapped by high capillary forces in the micron-sized pores in the reservoir rock or adsorbed onto mineral surfaces through irreducible oil saturation. There may also be pools of bypassed oil within the rock formations surrounding the main reservoir. Retrieving the normally immobile oil residing in the oil field after primary and secondary recovery is referred to herein as "tertiary recovery" or "enhanced oil recovery" (EOR).

Current EOR techniques may be able to remove an additional 5% to 20% of the oil remaining in a reservoir. Techniques currently available leave significant amounts of oil behind. Such techniques may also be expensive to carry out and inefficient. For example, bacteria may be used to free the oil trapped in rock pores or adsorbed onto mineral surfaces, and this freed oil may be dislodged with water during waterflooding. Such bacteria are introduced into the well from external sources. The bacteria may also create methane gas that can be recovered. As another example, gelled or crosslinked water-soluble polymers may be introduced that alter the permeability of geological formations to make waterflooding more effective. Polymers, either preformed or gelled/crosslinked in situ, may be introduced into the reservoir from external sources. Both bacterial techniques and polymer-based techniques are costly processes, though.

As another example, EOR may take place using a variety of externally-introduced chemical agents that may be used to increase the efficacy of waterflooding. These agents fall into two categories. One type of chemical agent may be a surfactant material that can alter the surface tension that adheres oil, water and rock together within the formation. The second type of chemical agent is viscous enough to slow the passage of water through the rock matrix so that the trapped oil can be pushed out more effectively. Chemical techniques for EOR may also be disadvantageous. Existing surfactants, for example, may adversely affect properties of oil-bearing rock formations and thereby damage reservoirs. Also, these surfactants, being of low viscosity, may not be effective in pushing the oil out of the pores where it is trapped. In addition, these surfactants may not be able to function effectively under the high temperature and high pressure conditions where they are used. Certain surfactants, such as petroleum sulfonates or their derivatives, are also particularly difficult to remove from the desired petroleum once it has been extracted. As an additional problem, surfactants are typically used with waterflooding techniques, leading to the production of highly stable emulsions containing mostly water with very little oil. In sum, with existing surfactant techniques, it is difficult to extract oil from rock and difficult to remove it from the water used to flush it out of the reservoir. The costs associated with these processes and their technical limitations have limited the widespread adaptation of these EOR techniques.

Many variations on the aforesaid systems and methods have been proposed. For example, U.S. Patent Appl. No. 20070079964 discloses the use of aliphatic anionic surfactants. U.S. Patent Appl. No. 20060046948 discloses the use of alkyl polyglycosides. U.S. Pat. No. 6,225,263 discloses the use of alkylglycol ethers. U.S. Pat. No. 6,475,290 discloses the use of lignin sulfonates. U.S. Pat. No. 5,911,276 discloses the use of lignin. U.S. Pat. No. 4,790,382 discloses the use of alkylated, oxidized lignin.

In addition to petroleum reservoirs as described above, petroleum may be extracted from formations called oil sands or tar sands. Oil sands, also called tar sands, are mixtures of sand or clay, water and extremely heavy crude oil (e.g., bitumen). For example, a major formation of oil sands in Alberta, Canada, contains material that is approximately 90% sand, 10% crude oil, and water. Oil sand formations are understood to comprise naturally-occurring petroleum deposits in which the lighter fractions of the oil have been lost, and the remaining heavy fractions have been partially degraded by bacteria. The crude oil is extra heavy crude and can be characterized as a naturally occurring viscous mixture of hydrocarbons that are generally heavier than pentane. The petroleum contained in these formations is a viscous, tar-like substance that is admixed with clay, sand and other inorganic particulate matter. Accordingly, it is harder to refine and generally of lesser quality than other crudes. While there is great variability, depending on the oil sands source, the mineral matter in oil sands typically includes a fairly uniform white quartz sand, silt, clay, water, bitumen and other trace minerals, such as zirconium, pyrite and titanium. The bitumen content of oil sands may be as high as 18%, or it can be substantially lower.

As described above, conventional crude oil in reservoirs may be readily extracted by boring wells into the formation, because the light or medium density oil in such reservoirs can flow freely out. By contrast, there is no free-flowing oil in an oil sand formation. Instead, these deposits must be strip mined or their petroleum content must be treated so that it flows.

In the strip mining method, oil sands are dug up from a surface mine and are transported and washed to remove the oil. Mining methods typically involve a number of steps, beginning with excavation and ore size reduction, followed by slurry formation with water and sodium hydroxide. The slurry is then treated with flotation agents (typically kerosene), frothing agents (methylisobutyl carbinol is common), and air is passed through the slurry to create a bitumen froth. This mixture is transported through approximately 2 kilometers of pipeline, creating a mechanical as well as chemical separation of the bitumen from the inorganic sand and silt. The pipeline leads to a separation tank that allows the froth to be skimmed off while the inorganic material falls to the bottom. Since the bitumen is much heavier than standard crude oil, it must be either mixed with a lighter petroleum or chemically processed so that it is flowable enough for transport. Further processing removes water and solids, following which the bitumen may be processed to form synthetic crude oil. Using this method, about two tons of tar sands produce one barrel of oil.

Much of the oil sands reserve is located below the surface, so the strip mining technique is not applicable. For these formations, a variety of in situ methods are available to extract bitumen from underground formations via specialized drilling and extraction techniques. These methods typically use a great amount of energy in the form of steam to heat the trapped bitumen. The heated bitumen has a lower viscosity and can then flow, slowly, to a production well. The steam-softened bitumen forms an emulsion with the water from the steam and drains to a wellhead within the formation from which it is pumped to the surface. This emulsion has similar characteristics to the water-bitumen emulsion produced during strip-mining. The emulsion may be treated similarly, with addition of NaOH and the application of petroleum solvents to make the material flowable.

Mining methods work well for "high-grade" oil sands, i.e., oil sands that have high bitumen content and low clay content. However, such high-grade materials afford a best-case scenario. In reality, the excavated oil sands exist as a mixture of high and low grade materials ("mixed-grade" oil sands). The "low-grade" materials with their lower bitumen content and high clay content are more difficult to extract using conventional methods. It tends to be impractical to separate the low-grade and the high-grade materials within mixed-grade oil sands, so the low-grade materials are simply carried along with the high-grade and not subjected to processing. Increasing production from this type of oil sand can create enormous opportunities for companies that have rights to less desirable grades of oil sands.

Many of the problems that affect oil production, such as those discussed above, also apply to environmental remediation following oil production and other environmental remediation problems, such as may exist following oil spills. Methods have been proposed for dealing with oil spills, such as those disclosed in U.S. Pat. No. 4,925,343 and U.S. Pat. No. 3,788,984.

As well, following petroleum production, there may be discharge of solid materials contaminated with petroleum products. In off-shore deep-water production, oil-laden mud that is wet with sea water must be barged to land, where energy-intensive processing takes place to allow stripping of oil from sand/clay particles and evaporation of water. Only after the mud is cleared of oil can it be dumped into landfill. Despite the inefficiencies, this production scheme is mandated by the EPA. Oil-soaked mud can not simply be put back into the ocean at the point of production without first making sure that all the adhered oil is removed. At present, no technology exists that permits ready stripping of oil from mud within the confines of a production platform.

Materials contaminated with petroleum, its byproducts or residues from its production can have substantial adverse impact on the environment. It would be advantageous to provide economical methods for treating such materials to remove the hydrocarbon contamination in a rapid and effective manner while avoiding the use of chemical or other agents that may inflict further damage on the environment.

SUMMARY

The invention relates to the discovery of certain surfactants that are capable of producing a petroleum based emulsion at a first pH and quickly demulsifying at a second pH. Thus the invention includes a petroleum recovery medium comprising a pH sensitive surfactant, said surfactant characterized by one or more hydrophobic region(s) or group(s) having an affinity to petroleum and a plurality of ionizable, hydrophilic group(s), the petroleum recovery medium being capable of (1) forming an emulsion with water and petroleum at a first pH and (2) demulsifying said emulsion at a second pH. Preferably, the surfactant is a carboxylated lignin, such as can be produced by reacting a lignin with an anhydride, such as a succinic anhydride or alkylated succinic anhydride. Preferred lignin include a kraft lignin characterized by hydroxyl groups. In one embodiment, between about 50 and 100% of the lignin hydroxyl groups are functionalized. Preferably, the surfactant forms the emulsion at a pH of about 7 and demulsifies at a pH of less than about 5. In embodiments, a hydrophilic polymer substituent, such as a polyethylene oxide and a polypropylene oxide, including a polyethylene oxide diglycidyl ether and a polypropylene oxide diglycidyl ether, is added to the surfactant. The hydrophilic polymer substituent preferably has a molecular weight between about 700 and 2500 g/mol. The surfactant can also be characterized by an inert substituent, such as a silicone, a siloxane, and a perfluorinated polymer, for example, added in an amount less than 25% by weight to the surfactant. In embodiments, the petroleum recovery material may be a drilling fluid.

For example, the surfactant can be produced by a process comprising reacting a lignin with a succinic acid anhydride, a hydrophilic polymer substituent selected from the group consisting of a polyethylene oxide diglycidyl ether and a polypropylene oxide diglycidyl ether and a siloxane. The invention also relates to a process of producing a carboxylated lignin surfactant comprising reacting a lignin with a succinic acid anhydride, a hydrophilic polymer substituent selected from the group consisting of a polyethylene oxide diglycidyl ether and a polypropylene oxide diglycidyl ether and a siloxane.

The invention also relates to a method of petroleum recovery, comprising:

(a) making an emulsion at a first pH comprising contacting petroleum, water and an emulsion producing amount of a petroleum recovery medium comprising a surfactant, said surfactant characterized by one or more hydrophobic region(s) or group(s) having an affinity to said petroleum and a plurality of ionizable, hydrophilic group(s), the petroleum recovery medium being capable of forming an emulsion with said water and said petroleum at said first pH;

(b) breaking the emulsion by changing the pH to a second pH;

(c) isolating the petroleum containing phase.

In embodiments, the method may include adding the petroleum recovery medium to a petroleum-containing underground formation. In embodiments, the method may include adding the petroleum recovery medium to a tar sand or oil sand. In embodiments, the method may include adding the petroleum recovery medium to oil laden debris.

DESCRIPTION

Disclosed herein are systems and methods useful in energy applications. In one embodiment, the invention provides for an amphiphilic petroleum recovery medium characterized by a surfactant comprising hydrophobic region(s) or group(s) having an affinity to hydrocarbon oils (e.g., particularly hydrocarbon groups, aromatic hydrophobic groups, lignin and its derivatives) and hydrophilic group(s), the petroleum recovery medium being capable of forming an emulsion with water (e.g., flood water or salt water) and a hydrocarbon oil (e.g., fossil fuels, such as bitumen) at the pH of use (e.g., within an oil deposit) and being capable of separation (e.g. breaking of an emulsion into two distinct phases) upon the modification of the pH (e.g., raising or lowering pH). That is, the preferred petroleum recovery media of the inventions comprise a compound which possess surfactant or emulsification properties at one pH and does not possess such properties at a second pH. In embodiments, petroleum recovery medium comprises a compound, as discussed above, wherein the hydrophobic region comprises a hydrocarbon and the hydrophilic region comprises an ionizable functional group which allows pH-induced switching.

The ionizable group can be cationic or anionic. Examples of cationic groups are preferably carbon containing acids, such as carboxylic acids. Sulfur containing acids, particularly stable sulfur containing acids, such as lignin sulfates and sulfonates, are excluded. Alternatively, applications could exist where ionizable groups such as amines (such as primary or secondary amines) or phosphines can be employed as the pH sensitive switching agent.

The petroleum recovery medium is preferably selected to contain atoms selected from the group consisting of carbon, hydrogen and oxygen, thereby avoiding the need for removing sulfur or nitrogen from the resulting product.

Acidic groups may be used to provide a hydrophilic portion for surfactant water stability. Such groups provide the switching ability necessary for the hydrophobic-hydrophilic transition leading to emulsification and demulsification of oil in water and water in oil mixtures. In an embodiment, the acids groups are derived from carboxylic acids. Preferably, the active surfactant mixture possesses surfactant properties (e.g., it readily forms an emulsion with water and the hydrocarbon oil) at a pH between about 5 and 9, preferably about 6 and 8, such as about 7 and does not possess such surfactancy (e.g., the phases separate) after pH modification. In an example where the ionizable group is an acid, this transition can occur at lower acidic pH values, preferably less than 5. If the ionizable group includes an amine functionality, this transition can occur upon raising the pH, preferably above 9. In embodiments, the character of the molecule, or surfactant properties, may be altered by changing the pH of the solution in which the surfactant resides.

Preferred petroleum recovery media of the invention comprise a compound characterized by a polymeric aromatic hydrophobic backbone. Such compounds of the invention can be made by reacting a first starting material, such as an aromatic hydrophobic polymer comprising a plurality of first functional groups, such as hydroxyl groups or amines, and a second starting material characterized by a second functional group which will react with said first functional group and cause a covalent bond to form and the presentation of an ionizable group. A preferred polymeric aromatic hydrophobic polymer includes lignins.

In embodiments, the systems and methods described herein may be useful for enhanced oil recovery. In embodiments, the petroleum recovery medium described herein may be useful as a drilling fluid or as a component thereof. In embodiments, the systems and methods described herein may be useful for environmental remediation or for recovery of petroleum from alternative sources, such as oil/tar sands.

As an example, modified lignins and formulations thereof may be useful for enhanced oil recovery, for environmental remediation and for the recovery of petroleum from alternative sources, such as oil/tar sands. Lignin may be modified, such as by the methods disclosed herein, to be compatible with a wide variety of hydrocarbons found in oil reservoirs. Lignins modified in accordance with these systems and methods may allow for an emulsion, such as a stable, low viscosity emulsion, to form when such modified lignins are exposed to oil-laden materials such as oil/tar sands, oil drilling waste and the like. The emulsion formed with these modified lignins may be destabilized at will, creating an easily recoverable, or separable, petroleum base. The recovery of mixtures of the highly aromatic and long-chain aliphatic hydrocarbons such as those found in heavy crude oil and bitumen may be termed petroleum recovery.

In embodiments, lignins may be used to provide the hydrophobic region of a surfactant. Lignin is a natural polymer which can be isolated from wood and wood products and is characterized by a hydrophobic backbone and hydroxyl groups, useful for further modification. Lignin and oxidized lignin are waste products from the paper industry. Oxidized lignin is described, for example, in U.S. Pat. No. 4,790,382 and is characterized by a plurality of hydroxyl groups which can be conveniently reacted. Similarly, kraft lignins, such as indulins, including Indulin AT, can be used to produce the petroleum recovery media of the invention. For example, the hydroxyl groups of such lignins can be reacted with an anhydride, such as succinic anhydride, and similar compounds to form a carboxylic acid-substituted lignin, by a ring opening reaction.

Lignin is a naturally-occurring polymer comprised of aliphatic and aromatic portions with alcohol functionality interspersed. Lignin polymers incorporate three monolignol monomers, methoxylated to various degrees: p-coumaryl alcohol, coniferyl alcohol, and sinapyl alcohol. These are incorporated into lignin in the form of the phenylpropanoids, p-hydroxyphenyl, guaiacyl, and syringal respectively. The systems and methods disclosed herein describe how naturally-occurring (i.e., native) and unnatural or modified lignin may be modified through functionalization of the resident alcohol moieties to alter the properties of the polymer, so that it may be adapted for petroleum recovery. Such a functionalized lignin may be termed a "modified lignin." The word "lignin", as used herein is intended to include natural and non-natural lignins which possess a plurality of lignin monomers and is intended to embrace lignin, kraft lignin, lignin isolated from bagasse and pulp, oxidized lignin, alkylated lignin, demethoxylated lignin, lignin oligomers, and the like.

Because lignin's chemical structure has similarity to the aromatic compounds found abundantly in heavy crude and tar sand, its modification and use as a tunable surfactant may be particularly effective in emulsifying such materials in petroleum recovery, for example as compared with generic surfactants such as sodium dodecyl sulfate (SDS) or ordinary soaps based on aliphatic tails. Other hydrophobic backbones which can be used to create the surfactants of the invention include complex aromatic hydrocarbon structures, such as polymerized tannins. In alternative embodiments, polysaccharides, such as cellulose can be used. Hydroxylated polystyrenes can be used as well.

In embodiments, adding a reactive agent such as succinic anhydride or alkylated succinic anhydride to a native lignin or other lignin may produce a modified lignin of the invention. Alkylated succinic anhydride is commonly used in the paper industry as a sizing agent. The alkyl additions are long chain hydrocarbons typically containing 16-18 carbon atoms. However, alkylated succinic acids having alkyl side chains having more than 1 carbon atom, such as 1 to 30 carbon atoms can be used as well. Such alkyl groups are defined herein to include straight chain, branched chain or cyclized alkyls as well as saturated and unsaturated alkyls. Examples of alkylated succinic anhydride include EKA ASA 200® (a mixture of C16 and C18 ASA) and EKA ASA 210® (a C18 ASA). Addition of an anhydride, such as a succinic anhydride or alkylated succinic anhydride to the resident alcohol groups result in new ester linkages and the formation of carboxylic acids via a ring opening mechanism. With the newly added carboxylic acid functionality, the modified lignin may obtain a particularly advantageous property: such modified lignins may be mixed with oil to form an emulsion that can be separated simply by the addition of a small amount of acid. In embodiments, adding acid to the oil-lignin emulsion removes the charge on the acid groups of the modified lignin, producing ionic destabilization that leads to rapid de-emulsification. In embodiments, the de-emulsification process can be measured in minutes, rather than weeks or even months without added acid.

In embodiments, addition of alkylated succinic anhydride to the resident alcohol groups in lignins may result in a new ester linkage and a carboxylic acid via a ring opening mechanism. With the newly added carboxylic acid functionality, the lignin becomes more water soluble. The incorporation of the alkane functionalities also imbues the compound with enhanced compatibility with lower molecular weight alkanes also present within the bitumen. By varying the composition of these additions, lignin can be adapted for a wide variety of bitumen compositions and inorganic components.

In other embodiments, the hydroxyl group resident on the hydrophobic polymer, or lignin, can be reacted with a dicarboxylic acid, such as maleic acid, or activated esters or anhydrides thereof to form a carboxylic acid substituted lignin. For example, the anhydride derived from many acids can be utilized, such as adipic acid. Further, activated esters can be used in place of the anhydride. Other examples will be apparent to those of ordinary skill in the art.

In yet other embodiments, polymers and copolymers characterized by functionalities with an affinity for aromatic fuel compounds, functionalities with an affinity fuel compounds and ionizable moieties can be used. For example, carboxylic acid containing polymers such as pectin or alginate, and the like, and synthesized polymers such as polyacrylic or methacrylic acid homo or co-polymers.

The degree of functionalization of the lignin (i.e., the percentage of hydroxyl groups that are reacted to present an ionic moiety) can be between 50% and 100%, preferably between 80% and 100% on a molar basis of the hydroxyl groups found on native lignins or a kraft lignin, such as Indulin AT®.

Where the ionizable functional group is a cation or amine, the group can be attached to the hydrophobic backbone by chemical methods generally known in the art. For example, the amine could be added to a lignin via a coupling agent, such as silane or diepoxide with a second subsequent reaction with a diamine or polyamine.

In other embodiments, lignin (oxidized or native) may be treated by chemically reacting it with reagents to tune the hydrophilicity to present alcohol groups. Examples of such reagents include hydrophilic molecules, or hydrophilic polymers, such as poly(ethylene glycol) (PEG) or poly(propylene glycol) (PPO) and combinations thereof. In a preferred embodiment, the hydrophilic polymer can have a molecular weight between 700 and 2500 g/mol Addition of PEG or PPO (with or without acidification) can be useful in stabilization of the product in salt solutions, particularly divalent cation salts. In this embodiment, the amount of polymer to lignin is preferably added in an amount between 25% and 75%.

An example of a chemical reaction includes:

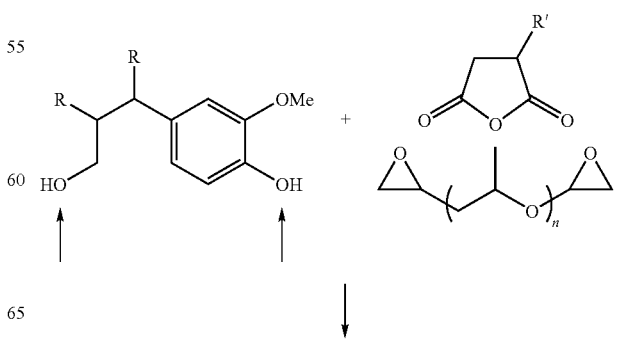

-continued

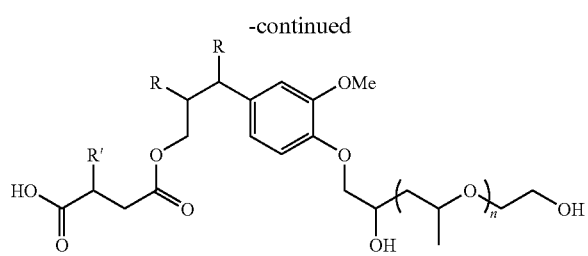

Other embodiments may include the chemical reaction of an inert component to prevent the compound from adsorbing or attracting to other materials within the oil formation, such as the rock. In this embodiment, silicones, siloxanes, such as poly(dimethylsiloxane) (PDMS), perfluorinated polymers (such as TEFLON®), polystyrenes or other hydrophobic polymers to increase the hydrophobicity of the lignin surfactant. Increasing the hydrophobicity of the surfactant can result in the reduction of surfactant loss within a oil formation comprising hydrophilic rock or geologies. Thus, grafting such hydrophobic polymers, such as PDMS, onto the lignin structure can be done, for example, to change the interaction of the surfactant with various petroleum and rock variations. The selection of the hydrophobic polymer and the amount thereof to be grafted can be determined empirically to adapt the surfactant to geologies that demonstrate high retention of the surfactant. By adding these chains, adsorption can be limited and the active concentration of surfactant to remain high. For example, PDMS can preferably be added to the lignin polymer in an amount between about 0 and 25% by weight.

It is desirable to control the molecular weight of the compound. Molecular weight ranges are preferably between about 500 and 3000, preferably about 1000 MW.

As described herein, the modified lignins may offer a basis for emulsification of residual petroleum in spent oil wells, or for emulsification of highly aromatic and aliphatic hydrocarbons such as those found in heavy crude oil and bitumen that exist, for example, in oil/tar sands, or for emulsification used as a technique for cleaning oil-laden debris. Each of these uses for the modified lignins, described in more detail herein, represents an example of petroleum recovery.

In embodiments, the petroleum recovery medium comprises a compound which acts as a surfactant that can solubilize oil resident in oil reservoirs and facilitate its removal at a first pH. After the oil has been recovered and transported to the ultimate collection site in an emulsion formed using such a surfactant, the pH of the solution may be altered, e.g., lowered, to disrupt the emulsion. This technology may permit the oil and water phase in the emulsion to separate and form a stratified system in a holding tank from which oil may be recovered. Using this technology, the surfactant may remain in the oil stock fraction. This is particularly preferred where the surfactant is free of nitrogen or sulfur. Due to the similar characteristics between the chemistry of the surfactant and the petroleum, the surfactant may be processed alongside with little hindrance to the upgrading procedures.

In embodiments, modified lignin solutions can also be formulated with other small molecule or polymeric surfactants and cosolvents to facilitate adaptation to various petroleum grades. These can be added to increase miscibility and emulsion formation or as additives for viscosity modifiers. Other additions can include hydrophobic polymers such as PDMS and the like that can tailor the properties according to the resident geology. Other modifications and applications of modified lignin solutions and formulations disclosed herein should be readily apparent to skilled artisans, using no more than routine experimentation.

Petroleum Recovery Technology

In embodiments, the systems and methods described herein may provide modified and unmodified lignins as extraction agents for enhanced oil recovery or for recovering petroleum from mixed grade oil sands. As used herein, the terms "oil sands" or "tar sands" refer to petroleum resources comprising mixtures of sand or clay, water, and petroleum, usually dense petroleum or bitumen. "Mixed grade" refers to oil sands that contain both high-grade oil sands with high bitumen content and low content of inorganic materials, and low-grade oil sands with low bitumen content and high content of inorganic materials.

In embodiments, modified lignins may be useful in combination with other processes for enhanced oil recovery (EOR). By injecting a portion, or "slug", of a waterborne lignin surfactant into an underground rock formation, residual oil can be stripped from the rock due to the decreased surface tension afforded by the surfactant, and propagated to a production well via subsequent water slugs. The surfactant slug may be comprised of some weight fraction of modified lignin, for example between 100 and 10,000 ppm concentration. It is generally desirable to minimize the amount of surfactant added to achieve an emulsion while minimizing cost. The term "effective amount," as used herein is defined to mean at least the amount of compound, or surfactant, required to achieve an emulsion at the conditions of use during oil extraction and can be empirically determined for each oil recovery site and application. Typically, the amount of surfactant required will be less than 1% by weight of the water slug, usually between 100 and 10,000 ppm, preferably between 5,000 and 10,000 ppm. Additionally, other additives known in the art can be added as viscosity modifiers and/or corrosion inhibitors, and the like.

Though it is understood that the majority (80-90%) of the oil will be produced ahead of the surfactant slug, a portion remains as a mixture with the surfactant. Technology utilizing surfactant slugs is described in L. W. Lake, *Enhanced Oil Recovery*, (Prentice Hall, 1989), the contents of which are included herein by reference. Rather than discarding this fraction or risk contamination of downstream refining equipment, an emulsion formed with modified lignins and other compounds described herein as surfactants can be rapidly separated by modifying pH, such as by the addition of a protic acid, to break the emulsion and create a preliminary petroleum purification. Examples of suitable strong protic acids that can be used in breaking the emulsion or separating the aqueous and oil phases includes, but is not limited to, hydrochloric and sulfuric acids.

In embodiments, the novel surfactants, or modified lignins, may be useful for recovering petroleum in a useful form from mixed grades of oil sands, as well as from high-grade oil sands. Using a process aid based on a modified lignin, these oil sands may be made more productive. Addition of hydrophilic moieties to the aliphatic and phenolic alcohol functional groups present on the polymer can give it increased water solubility. The base lignin, structurally similar to bitumen, helps to strip the petroleum product from inorganic materials, such as those found in oil sands applications.

In embodiments, the novel surfactants, or modified lignins, modified by the methods disclosed herein may be used to strip tar/oil sands of their residual oil. Using these compositions and methods, petroleum residing on the bituminous ore can be recovered as a lower viscosity water emulsion. The resulting emulsion can then be easily transported to refining centers for further processing, unlike concentrated bitumen. In embodiments, modified lignins may possess a tunable phase separation property that facilitates water removal from this mixture.

In embodiments, addition of alkylated succinic anhydride to the resident alcohol groups in lignins may result in a new ester linkage and a carboxylic acid via a ring opening mechanism. With the newly added carboxylic acid functionality, the lignin becomes more water soluble. The incorporation of more alkane functionalities also imbues the polymer with enhanced compatibility with lower molecular weight alkanes also present within the bitumen. By varying the composition of these additions, lignin can be adapted for a wide variety of bitumen compositions and inorganic components.

In embodiments, modified or unmodified lignin solutions can also be formulated with other small molecule or polymeric surfactants and cosolvents to facilitate adaptation to various bitumen grades. These can be added to increase miscibility and emulsion formation or as additives for viscosity modifiers. By varying the composition of these additions, lignin can be adapted for a wide variety of bitumen compositions and inorganic components. In embodiments, modified or unmodified lignin solutions can also be formulated with other small molecule or polymeric surfactants and cosolvents to facilitate adaptation to various bitumen grades. These can be added to increase miscibility and emulsion formation or as additives for viscosity modifiers.

Environmental Remediation

In embodiments, systems and methods are provided herein for producing formulations having applications in the field of oil extraction, both for well development operations such as drilling operations, work-over operations or completion operations and for oilfield production proper. As described herein, the novel surfactants, or modified lignins, modified for use in environmental remediation and oil recovery may allow for a stable, low viscosity emulsion that can be destabilized at will, creating an easily recoverable petroleum base. In embodiments, the novel surfactants, or modified lignins, may be useful for cleaning oil-laden debris or for recovering emulsified petroleum products.

In embodiments, the novel surfactants, or modified lignins, may be used alone or with other components in a solution used to extract the oil that coats the debris produced during the drilling process. Properties of the novel surfactants, or modified lignins, may include increased hydrocarbon solubility and the ability to emulsify hydrocarbons in aqueous solution. Certain modifications as disclosed herein may be particularly advantageous for recovering oil from oil drilling debris and the like, for example, by means of pH adjustment inducing phase separation of the emulsion. As described herein, tunable induction of phase separation may be advantageously substituted for present, more expensive treatment methods such as dessication and other isolation procedures.

EXAMPLES

Example 1

Indulin AT is used as the lignin source. Indulin AT is a purified form of the lignin obtained from the black liquor in the Kraft pulping process. Here, Indulin AT (5.0 g) is suspended in 150 ml of acetone. Alkylated succinic anhydride in the form of Eka SA 210 (25.0 g) is added to the suspension. The reaction is performed in a bomb and heated to 70° C. over the course of 48 hours. The resulting material can be diluted with alkaline water and used as a suitable surfactant for stripping oil from debris produced as a byproduct of drilling. Oil coated debris is then exposed to the brown aqueous dispersion in a 1:1 weight ratio for several seconds with agitation. Afterwards, the liquid portion is decanted from the now clean debris. Acid is then added to the separated liquid to induce phase separation.

Example 2

Indulin AT (5.0 g) is mixed with 10.0 g Eka SA 210 in a bomb filled with 150 ml of acetone. The mixture is heated to 70° C. over 48 hours, and the recovered product is diluted with alkaline water for an active product. Oil coated debris is then exposed to the brown aqueous dispersion in a 1:1 weight ratio for several seconds with agitation. Afterwards, the liquid portion is decanted from the now clean debris. Acid is then added to the separated liquid to induce phase separation.

Example 3

Indulin AT (5.0 g) is mixed with 5.0 g Eka SA 210 in a bomb filled with acetone. The mixture is heated to 70° C. over 48 hours. The resulting mixture is filtered; the supernatant is recovered and diluted with alkaline water to create an active product. Oil coated debris is then exposed to the brown aqueous dispersion in a 1:1 weight ratio for several seconds with agitation. Afterwards, the liquid portion is decanted from the now clean debris. Acid is then added to the separated liquid to induce phase separation. The debris can then be tested for residual oil content.

Example 4

Indulin AT (5.0 g) is mixed with 4.0 g Eka SA 210 in a bomb filled with 150 ml of acetone. The mixture is heated to 70° C. over 48 hours. The resulting mixture is filtered; the supernatant is recovered and diluted with alkaline water to create an active product. Oil coated debris is then exposed to the brown aqueous dispersion in a 1:1 weight ratio for several seconds with agitation. Afterwards, the liquid portion is decanted from the now clean debris. Acid is then added to the separated liquid to induce phase separation. The debris can then be tested for residual oil content.

Example 5

Indulin AT (5.0 g) is mixed with 3.0 g Eka SA 210 in a bomb filled with 150 ml of acetone. The mixture is heated to 70° C. over 48 hours. The resulting mixture is filtered; the supernatant is recovered and diluted with alkaline water to create an active product. Oil coated debris is then exposed to the brown aqueous dispersion in a 1:1 weight ratio for several seconds with agitation. Afterwards, the liquid portion is decanted from the now clean debris. Acid is then added to the separated liquid to induce phase separation. The debris can then be tested for residual oil content.

Example 6

Indulin AT (5.0 g) is mixed with 2.5 g Eka SA 210 in a bomb filled with 150 ml of acetone. The mixture is heated to 70° C. over 48 hours. The resulting mixture is filtered; the supernatant is recovered and diluted with alkaline water to create an active product. Oil coated debris is then exposed to the brown aqueous dispersion in a 1:1 weight ratio for several seconds with agitation. Afterwards, the liquid portion is decanted from the now clean debris. Acid is then added to the separated liquid to induce phase separation. The debris can then be tested for residual oil content.

Example 7

Indulin AT (5.0 g) is mixed with 1.0 g Eka SA 210 and 3.0 g succinic anhydride in a bomb filled with 150 ml of acetone. The mixture is heated to 70° C. over 48 hours. The resulting mixture is filtered; the supernatant is recovered and diluted with alkaline water to create an active product. Oil coated debris is then exposed to the brown aqueous dispersion in a 1:1 weight ratio for several seconds with agitation. Afterwards, the liquid portion is decanted from the now clean debris. Acid is then added to the separated liquid to induce phase separation. The debris can then be tested for residual oil content.

Example 8

Indulin AT (5.0 g) is mixed with 2.0 g Eka SA 210 and 2.0 g succinic anhydride in a bomb filled with 150 ml of acetone. The mixture is heated to 70° C. over 48 hours. The resulting mixture is filtered; the supernatant is recovered and diluted with alkaline water to create an active product. Oil coated debris is then exposed to the brown aqueous dispersion in a 1:1 weight ratio for several seconds with agitation. Afterwards, the liquid portion is decanted from the now clean debris. Acid is then added to the separated liquid to induce phase separation. The debris can then be tested for residual oil content.

Example 9

Indulin AT (5.0 g) is mixed with 3.0 g Eka SA 210 and 1.0 g succinic anhydride in a bomb filled with 150 ml of acetone. The mixture is heated to 70° C. over 48 hours. The resulting mixture is filtered; the supernatant is recovered and diluted with alkaline water to create an active product. Oil coated debris is then exposed to the brown aqueous dispersion in a 1:1 weight ratio for several seconds with agitation. Afterwards, the liquid portion is decanted from the now clean debris. Acid is then added to the separated liquid to induce phase separation. The debris can then be tested for residual oil content.

Example 10

Indulin AT (5.0 g) is mixed with 4.0 g Eka SA 210 and 1.0 g polyethylene glycol diglycidyl ether in a bomb filled with 150 ml of acetone. The mixture is heated to 70° C. over 48 hours. The resulting mixture is filtered; the supernatant is recovered and diluted with alkaline water to create an active product. Oil coated debris is then exposed to the brown aqueous dispersion in a 1:1 weight ratio for several seconds with agitation. Afterwards, the liquid portion is decanted from the now clean debris. Acid is then added to the separated liquid to induce phase separation. The debris can then be tested for residual oil content.

Example 11

Indulin AT (5.0 g) is mixed with 3.0 g Eka SA 210 and 1.0 g polypropylene oxide diglycidyl ether in a bomb filled with 150 ml of acetone. The mixture is heated to 70° C. over 48 hours. The resulting mixture is filtered; the supernatant is recovered and diluted with alkaline water to create an active product. Oil coated debris is then exposed to the brown aqueous dispersion in a 1:1 weight ratio for several seconds with agitation. Afterwards, the liquid portion is decanted from the now clean debris. Acid is then added to the separated liquid to induce phase separation.

Example 12

Lignin derivatives based on Indulin AT were prepared following the procedures listed in the previous examples for each derivative described below. Each lignin derivative was dissolved in water with minimal addition of concentrated sodium hydroxide solution (6M, about 1 ml) at a 1 wt % concentration. The resulting surfactant solution was then placed in a container with oil sands (4 g) to create a slurry with 10-30% solid content by weight. Aeration was performed on the slurry along with mechanical stirring. The bubbles created were allowed to flow in an exterior dish for collection of any bitumen carried by the bubbles. After several minutes of aeration and agitation, the sample dish was then drained of fluids, and the resulting sand was analyzed for residual bitumen content via combustion. The following results were obtained:

Sample 1: Using a surfactant with the composition of Indulin AT modified with 20 weight percent poly(dimethylsiloxane) and 80 weight percent Eka SA 210 alkylated succinic anhydride to extract bitumen from a low-grade oil sand sample (4 g):
    2.78 g remaining solids (8% bitumen content)
    0.59 g clean bitumen removed.

Sample 2: Using a surfactant with the composition of Indulin AT modified with 20 weight percent poly(dimethylsiloxane) and 80 weight percent Eka SA 210 alkylated succinic anhydride to extract bitumen form a high-grade oil sand sample (4 g):
    3.229 g remaining solids (9% bitumen content)
    0.542 g clean bitumen removed.

Sample 3: Using a surfactant with the composition of Indulin AT modified with 20 weight percent poly(propylene oxide) and 80 weight percent Eka SA 210 alkylated succinic anhydride to extract bitumen form a low-grade oil sand sample (4 g):
    2.7602 g remaining solids (4% bitumen content)
    0.6786 g clean bitumen removed.

For comparison, the oil sands sample received was approximately 10% bitumen content. A high bitumen content sample obtained from a different source was approximately 15% bitumen content.

Each patent, patent application and publication referenced or discussed above is hereby incorporated by reference in its entirety.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:

1. A petroleum recovery medium comprising water and a pH sensitive surfactant, said surfactant characterized by one or more hydrophobic region(s) or group(s) having an affinity to petroleum and a plurality of ionizable, hydrophilic groups and wherein said surfactant is a modified lignin, the petroleum recovery medium being capable of (1) forming an emulsion with water and petroleum at a first pH and (2) demulsifying said emulsion at a second pH, wherein at least some of said ionizable hydrophilic groups include an ester linkage and a carboxylic acid functional group.

2. The medium in accordance with claim 1 wherein the surfactant is produced by reacting a lignin with an anhydride.

3. The medium in accordance with claim 2 wherein the anhydride is a succinic anhydride.

4. The medium in accordance with claim 3 wherein the anhydride is an alkylated succinic anhydride.

5. The medium in accordance with claim 2 wherein the lignin is a kraft lignin characterized by hydroxyl groups.

6. The medium in accordance with claim 5 wherein between about 50 and 100% of the hydroxyl groups are functionalized.

7. The medium in accordance with claim 1 wherein the surfactant forms the emulsion at a pH of about 7 and demulsifies at a pH of less than about 5.

8. The medium in accordance with claim 1 wherein the lignin is further characterized by a hydrophilic polymer substituent.

9. The medium in accordance with claim 8 wherein the hydrophilic polymer substituent is selected from the group consisting of a polyethylene oxide and a polypropylene oxide.

10. The medium in accordance with claim 9 wherein the hydrophilic polymer substituent is selected from the group consisting of a polyethylene oxide diglycidyl ether and a polypropylene oxide diglycidyl ether.

11. The medium in accordance with claim 10 wherein the hydrophilic polymer substituent has a molecular weight between about 700 and 2500 g/mol.

12. The medium in accordance with claim 11 wherein the inert substituent is selected from the group consisting of a silicone, a siloxane, and a perfluorinated polymer.

13. The medium in accordance with claim 1 wherein the lignin is further characterized by an inert substituent.

14. The medium in accordance with claim 13 wherein the inert substituent is a siloxane and is added in an amount less than 25% by weight to the surfactant.

15. The medium in accordance with claim 1 comprising a surfactant produced by a process comprising reacting a lignin with a succinic acid anhydride, a hydrophilic polymer substituent selected from the group consisting of a polyethylene oxide diglycidyl ether and a polypropylene oxide diglycidyl ether and a siloxane.

16. The medium in accordance with claim 1 wherein the medium is a drilling fluid.

17. A process of producing a carboxylated lignin surfactant comprising reacting a lignin with a succinic acid anhydride, a hydrophilic polymer substituent selected from the group consisting of a polyethylene oxide diglycidyl ether and a polypropylene oxide diglycidyl ether and a siloxane.

18. A method of petroleum recovery, comprising:
  (a) making an emulsion at a first pH comprising contacting petroleum and an emulsion producing amount of a petroleum recovery medium comprising water and a surfactant, said surfactant characterized by one or more hydrophobic region(s) or group(s) having an affinity to said petroleum and a plurality of ionizable, hydrophilic group(s), the drilling fluid being capable of forming an emulsion with said water and said petroleum at said first pH;
  (b) breaking the emulsion by changing the pH to a second pH;
  (c) isolating the petroleum containing phase.

19. The method of petroleum recovery in accordance with claim 18 wherein the petroleum recovery medium is added to a petroleum-containing underground formation.

20. The method of petroleum recovery in accordance with claim 18 wherein the petroleum recovery medium is added to a tar sand or oil sand.

21. The method of petroleum recovery in accordance with claim 18 wherein the petroleum recovery medium is added to oil laden debris.

22. A petroleum recovery medium comprising water and a pH sensitive surfactant, said surfactant characterized by one or more hydrophobic region(s) or group(s) having an affinity to petroleum and a plurality of ionizable, hydrophilic groups and wherein said surfactant is a modified lignin, the petroleum recovery medium being capable of (1) forming an emulsion with water and petroleum at a first pH and (2) demulsifying said emulsion at a second pH, wherein at least some of said ionizable, hydrophilic groups includes a carboxylic acid functional group and wherein said lignin is further substituted with a hydrophilic polymer substituent.

* * * * *

UNITED STATES PATENT AND TRADEMARK OFFICE
CERTIFICATE OF CORRECTION

| | | |
|---|---|---|
| PATENT NO. | : 7,871,963 B2 | Page 1 of 1 |
| APPLICATION NO. | : 11/850749 | |
| DATED | : January 18, 2011 | |
| INVENTOR(S) | : Kristoffer K. Stokes et al. | |

It is certified that error appears in the above-identified patent and that said Letters Patent is hereby corrected as shown below:

Under Column 16, Claim 17, line 12: "carboxylated" should be replaced with --modified--.

Under Column 16, Claim 18, line 21: after "said surfactant" --is modified lignin and is-- should be inserted.

Under Column 16, Claim 18, line 24: after "group(s)," --that include an ester linkage and a carboxylic acid functional group wherein a-- should be inserted and "the" should be deleted.

Signed and Sealed this
Twelfth Day of April, 2011

David J. Kappos
*Director of the United States Patent and Trademark Office*